(12) United States Patent
Ziegler et al.

(10) Patent No.: US 6,525,092 B1
(45) Date of Patent: Feb. 25, 2003

(54) PESTICIDAL BIS-OXIME COMPOUNDS

(75) Inventors: Hugo Ziegler, Witterswil (CH); Stephan Trah, Freiburg (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/787,481

(22) PCT Filed: Sep. 20, 1999

(86) PCT No.: PCT/EP99/06954

§ 371 (c)(1),
(2), (4) Date: Apr. 27, 2001

(87) PCT Pub. No.: WO00/17155

PCT Pub. Date: Mar. 30, 2000

(30) Foreign Application Priority Data

Sep. 22, 1998 (GB) ............................................. 9820583
Jan. 7, 1999 (GB) ............................................. 9900293

(51) Int. Cl.⁷ ..................... A01N 37/34; C07C 255/00
(52) U.S. Cl. .................... 514/524; 514/525; 558/418; 558/419; 558/423
(58) Field of Search ................................ 558/418, 419, 558/423; 514/524, 525

(56) References Cited

U.S. PATENT DOCUMENTS

| 5,965,613 | A | | 10/1999 | Isenring et al. ............ 514/538 |
| 6,156,923 | A | * | 12/2000 | Farooq et al. |
| 6,255,352 | B1 | * | 7/2001 | Grammenos et al. |

FOREIGN PATENT DOCUMENTS

| EP | 0 498 188 | 8/1992 |
| WO | 95/18789 | 7/1995 |
| WO | 97/20809 | 6/1997 |
| WO | 98/53682 | 3/1998 |
| WO | 98/28262 | 7/1998 |

OTHER PUBLICATIONS

*Chemical Abstracts, vol. 95, No. 21, Nov. 23, 1981, Abstract No. 186778z, J. Berger et al: "Syntheisi of Some New Phenyl–1, 2–Alkanedione Dioximes" p. 611, col. 2; XP002125629, abstract & J. Prakt. Chem. vol. 323, No. 1, 1981, pp. 137–148, Freiberg, Germany.

*Joseph Wiemann et al: "Synthèse de Composés Hétérocycliques à noyaux Pyrazined", Comptes Rendus Hebdomadaires Des Seances DE L'Academie Des Sciences., vol. 263, No. 8, Aug. 22, 1966, pp. 608–611, XP002125628, Gauthier–Villars. Montreuil., FR p. 609, line 7–line 11.

*Werner Jugelt et al: "Untersuchungen zur Regioselektivität der anodischen cyclsierung von 1,2–Dioximem zu unsymmetrisch substituierten Furoxanen" Zeitschrift Für Chemie, vol. 23, No. 1, 1981, pp. 29–30, XP000863708, Leipzig, DE p. 29, table 2, compound 1b; p. 30, col. 2, first reaction scheme.

* cited by examiner

Primary Examiner—Johann Richter
Assistant Examiner—Paul A. Zucker
(74) Attorney, Agent, or Firm—Richard E. L. Henderson; Joseph C. Gil; John E. Mrozinski

(57) ABSTRACT

Bis-oxime compounds of the general formula (I) are provided

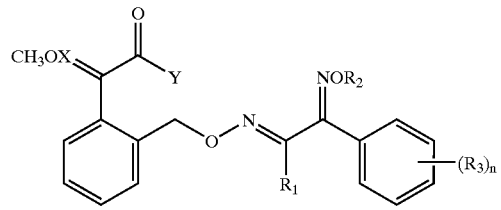

wherein X, Y, $R_1$, $R_2$, $R_3$ and n are as defined in the specification. The bis-oxime compounds possess pesticidal activity, which may provide plants with protection from phytopathogenic microorganisms.

3 Claims, No Drawings

PESTICIDAL BIS-OXIME COMPOUNDS

This application is a 37-1 of PCT/EP99/06954 filed Sep. 20, 1999.

The invention relates to novel pesticidally, in particular fungicidally, active bis-oxime compounds of formula I

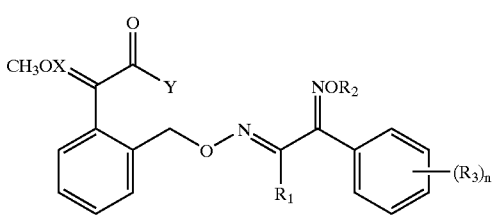

wherein a) X is CH, and Y is $OCH_3$, or b) X is N, and Y is $OCH_3$, $OC_2H_5$ or $NHCH_3$;

$R_1$ is ethyl or cyclopropyl;

$R_2$ is hydrogen, methyl or ethyl;

$R_3$ is cyano;

n is 1 or 2.

The formula I embraces all stereoisomeric forms and mixtures thereof, such as racemic and diasteromeric mixtures, for example E/Z mixtures.

1,2-Dioxime ether derivatives having fungicidal activities are known, e.g. from WO 95/18789. It has been found that the compounds according to the invention exhibit improved biological properties which render them very suitable for practical use in agriculture and horticulture by having an extraordinarily good fungicidal activity, especially in cereals.

The invention furthermore relates to the preparation of these compounds, to agrochemical compositions which comprise, as active ingredients, at least one of these compounds, and to the use of the active ingredients or of the compositions for protecting plants against attack by harmful microorganisms, in particular fungi, as well as to intermediates and their preparation.

Preferred groups are (a) compounds wherein in formula I $R_2$ is methyl or ethyl;

$R_3$ is cyano.

(b) compounds wherein in formula I

X is N, and Y is $OCH_3$, or $NHCH_3$;

$R_2$ is methyl;

$R_3$ is 4-cyano.

Also preferred are the compounds of the Tables, in particular compound No. 1.3

The compounds of formula I can be prepared as follows:

A) To obtain a compound of formula I wherein X, Y, $R_1$, $R_3$ and n are as defined for formula I and $R_2$ is methyl or ethyl:

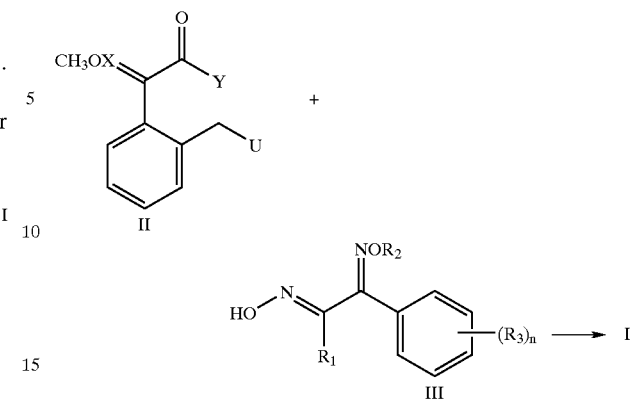

A compound of formula II, wherein the substituents are as defined for formula I and U is a leaving group, for example chlorine, bromine, iodine, mesyloxy or tosyloxy, is reacted with a compound of formula III, wherein the substituents are as defined above, preferably in an organic solvent in presence of a base.

B) To obtain a compound of formula I, wherein X, Y, $R_1$, $R_3$ and n are as defined for formula I and $R_2$ is hydrogen (formula I.b):

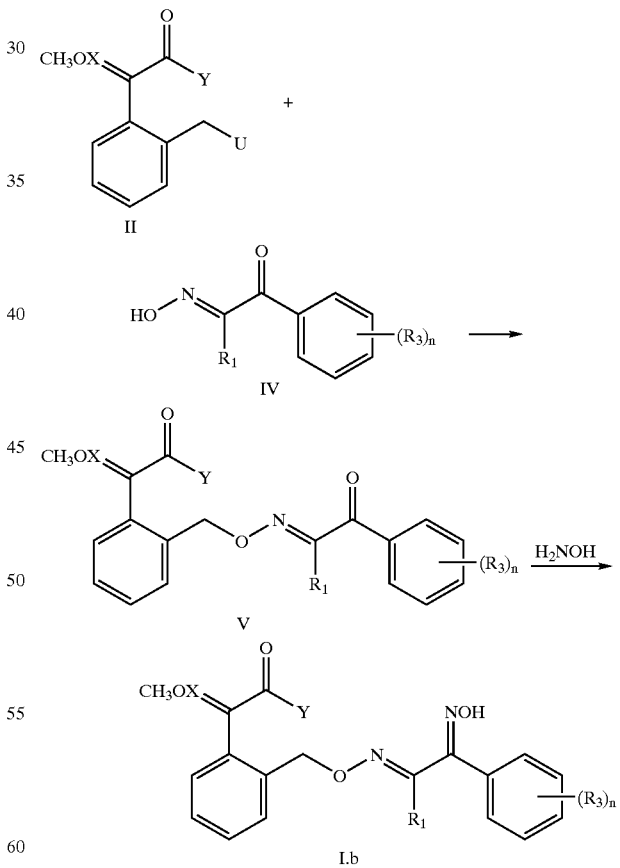

In an analogous reaction as described under A), compounds of formula II and IV, wherein the substituents are as defined under A) above, are reacted to give a compound of formula V which is further reacted with $H_2NOH$ to give a compound of formula I.b.

C) To obtain a compound of formula I, wherein X is N and Y is NHCH$_3$: A compound of formula I, wherein X is N and Y is OCH$_3$ or OC$_2$H$_5$ is reacted in a solvent with NH$_2$CH$_3$.

Compounds of formula II are known, e.g. from WO95/18789.

Compounds of formulae III, wherein R$_1$, R$_2$, R$_3$ and n are as defined for formula I are part of the present invention and can be prepared as follows:

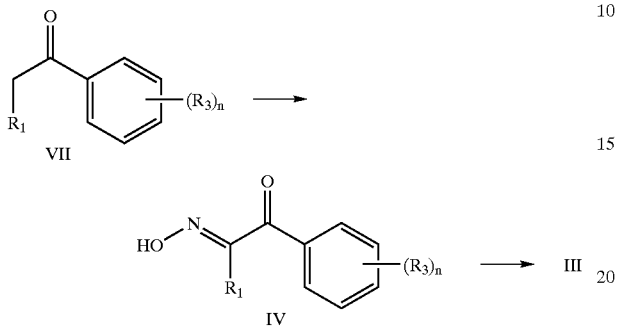

(a) Reacting a compound of formula VII, wherein the substituents are as defined for formula I, with nitrous acid or with an organic nitrite, e.g. a C$_1$-C$_6$alkyl nitrite such as pentyl nitrite, to give a compound of formula IV, which is converted to a compound of formula III (b1) either directly with O-methylhydroxylamine or with O-ethylhydroxylamine respectively, or a salt thereof, as the hydrochloride or sulfate or phosphate, to give a compound of formula III wherein R$_2$ is methyl or ethyl;

(b2) or with hydroxylamine or a salt thereof, as the hydrochloride or sulfate or phosphate, or with hydroxylamin-O-sulfonic acid, to give a compound of formula III, wherein R$_2$ is hydrogen, and optionally converting this 1,2-dioxime with a methylating or ethylating agent respectively, for example with methyl iodide or dimethyl sulfate; or ethyl iodide or diethyl sulfate respectively, to give a compound of formula III, wherein R$_2$ is methyl or ethyl.

E)

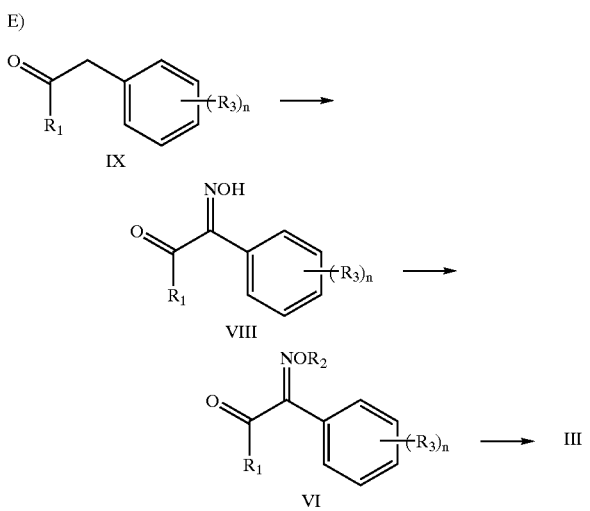

(a) Reacting a compound of formula IX, wherein the substituents are as defined for formula I, with nitrous acid or with an organic nitrite, e.g. a C$_1$-C$_6$alkyl nitrite such as pentyl nitrite, to give a compound of formula VIII;

(b) converting the compound of formula VIII with a methylating or ethylating agent respectively, for example with methyl iodide or dimethyl sulfate; or ethyl iodide or diethyl sulfate respectively, to give a compound of formula VI, wherein R$_2$ is methyl or ethyl;

(c) converting the compound of formula VI with hydroxylamine or a salt thereof, as the hydrochloride or sulfate or phosphate, or with hydroxylamin-O-sulfonic acid, to give a compound of formula III.

Compounds of formula VII and IX are known or may be prepared by known methods. The compounds of formula I can be used in the agricultural sector and related fields preventively and/or curatively as active ingredients in the control of plant diseases. The compounds of formula I according to the invention are distinguished by having good activity even at low rates of concentration, by being well tolerated by plants and by being environmentally friendly. They possess very advantageous, especially systemic, properties and can be used for the protection of a large number of cultivated plants. With the compounds of formula I it is possible to inhibit or destroy the pests that occur on plants or on parts of plants (the fruit, blossom, leaves, stems, tubers or roots) of various crops of useful plants, while parts of plants that grow later are also protected against phytopathogenic microorganisms, in particular fungi.

The compounds I can also be used as dressings in the treatment of seed (fruit, tubers, grains) and plant cuttings to provide protection against fungus infections as well as against phytopathogenic fungi that occur in the soil.

The compounds I are effective, for example, against phytopathogenic fungi belonging to the following classes: Fungi imperfecti (e.g. Botrytis, Pyricularia, He dimethyl sulfate Iminthosporium, Fusarium, Septoria, Cercospora und Alternaria); Basidiomycetes (e.g. Rhizoctonia, Hemileia, Puccinia); Ascomycetes (e.g. Venturia and Erysiphe, Podosphaera, Monilinia, Uncinula) and Oomycetes (e.g. Phytophthora, Pythium, Plasmopara).

Within the scope of the invention, target crops for plant protection use include, for example, the following species of plants: cereals (wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); and plants such as tobacco, nuts, coffee, aubergines, sugar cane, tea, pepper, vines, hops, bananas and natural rubber plants, as well as ornamentals.

The compounds I are usually used in the form of compositions and can be applied to the area or plant to be treated simultaneously or in succession with further active ingredients. These further active ingredients may be, for example, fertilisers, micronutrient donors or other preparations that influence plant growth. It is also possible to use selective herbicides, and insecticides, fungicides, bactericides, nematicides, molluscicides or mixtures of several of these preparations, if desired together with further carriers, surfactants or other application-promoting adjuvants customarily employed in formulation technology. Suitable carriers and adjuvants may be solid or liquid and are the substances usefully employed in formulation technology, for example natural or regenerated mineral substances, solvents, dispersants, wetting agents, tackifiers, thickeners, binders or fertilisers.

A preferred method of applying a compound of formula I, or an agrochemical composition comprising at least one of those compounds, is application to the foliage of the plants (foliar application). The frequency and the rate of application depend upon the risk of infestation by the pathogen in question. However, the compounds of formula I can also penetrate the plants through the roots via the soil (systemic action) if the locus of the plants is impregnated with a liquid formulation or if the active ingredients are incorporated into the soil in solid form, e.g. in granular form (soil application). In the case of paddy rice crops, such granules may be applied in metered amounts to the flooded rice field. The compounds of formula I may, however, for seed treatment, also be applied to the seed grains (coating), either by impregnating the seeds or tubers with a liquid formulation of the active ingredient or by coating them with a solid formulation.

The compounds of formula I are used in unmodified form or, preferably, together with the adjuvants conventionally employed in formulation technology. For that purpose they are advantageously formulated in known manner e.g. into emulsifiable concentrates, coatable pastes, directly sprayable or dilutable solutions, dilute emulsions, wettable powders, soluble powders, dusts or granules, for example by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are generally from 1 g to 2 kg of active ingredient (a.i.) per hectare (ha), preferably from 10 g to 1 kg a.i./ha, especially from 20 g to 600 g a.i./ha. When used as seed dressings, rates of from 10 mg to 1 g of active ingredient per kg of seed are advantageously used.

The formulations, i.e. the compositions, preparations or mixtures comprising the compound active ingredient) of formula I and, where appropriate, a solid or liquid adjuvant, are prepared in known manner, e.g. by homogeneously mixing and/or grinding the active ingredient with extenders, such as solvents, solid carriers and, where appropriate, surface-active compounds (surfactants).

The agrochemical compositions normally comprise 0.1 to 99% by weight, especially 0.1 to 95% by weight, compound of formula I, 99.9 to 1% by weight, especially 99.8 to 5% by weight, of a solid or liquid adjuvant, and 0 to 25% by weight, especially 0.1 to 25% by weight, of a surfactant.

The compounds of formula I can be mixed with other fungicides, producing in some cases unexpected synergistic effects.

Especially preferred mixing partners are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodione, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxyl}-o-tolyl]-glyoxylic acid-methylester-O-methyloxime (trifloxystrobin); dithiocarbamates such as ferbam, mancozeb, maneb, meti ram, propineb, thi ram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethotencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-dihydroimidazol-4-one (RPA 407213), 3,5-dichloro-N-(3-chloro-1-ethyl-1 -methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042), or iprovalicarb (SZX 722).

1. Preparation Examples

EXAMPLE P-1

Preparation of Compound No. 1.1.

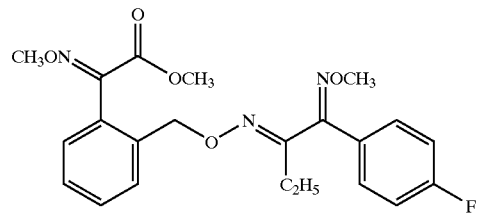

0.2 g of a 60% sodium hydride dispersion in mineral oil is washed with hexane, and 5 ml of N,N-dimethylformamide are added thereto. To that suspension there are added 1.5 g of 2-(bromomethylphenyl)glyoxylic acid methyl ester O-methyl oxime and 1.2 g of 1-(4-fluorophenyl)-butane-1,2-dione-1-(O-methyloxime)-2-oxime. The reaction mixture is heated to 50° C. and stirred at room temperature for one hour. Ice-water is then added and extraction is carried out twice with 50 ml of ethyl acetate each time. The combined organic extracts are washed with water and dried over sodium sulfate and the solvent is distilled off under reduced pressure. The residue is purified by chromatography on silica gel using ethyl acetate/hexane (1:5% by volume to 1:4% by volume). 1.3 g of the desired product are obtained in the form of a colourless oil.

EXAMPLE P-2

Preparation of Compound No. 1.12.

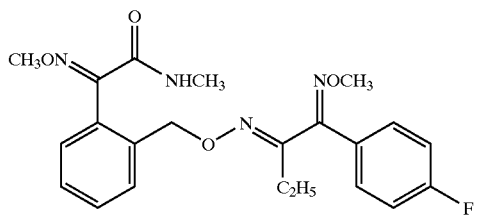

The compounds of the following tables may be obtained in analogous manner.

1.1 g of the compound No. 1.1 obtained in P-1 are stirred in 15 ml of a 33% ethanolic methylamine solution for 1 hour at room temperature. Ethanol and excess methylamine are distilled off and the residue is filtered over silica gel using diethyl ether. The product is obtained in the form of crystals, m.p. 129–131° C.

TABLE 1

| No. | X | Y | $R_2$ | $R_3$ | phys. data (m.p. ° C.) |
|---|---|---|---|---|---|
| 1.1. | N | $OCH_3$ | $CH_3$ | 4-F | oil |
| 1.2. | N | $NHCH_3$ | $CH_3$ | 4-F | 129–131 |
| 1.3. | N | $NHCH_3$ | $CH_3$ | 4-CN | 138–141 |
| 1.4. | CH | $OCH_3$ | $CH_3$ | 4-CN | |
| 1.5. | N | $OCH_3$ | $CH_3$ | 4-CN | |
| 1.6. | N | $OCH_3$ | $CH_3$ | 4-CN | |
| 1.7. | N | $OCH_3$ | H | 4-CN | |
| 1.8. | N | $OC_2H_5$ | H | 4-CN | |
| 1.9. | N | $NHCH_3$ | H | 4-CN | |

TABLE 2

| No. | X | Y | $R_2$ | $R_3$ | phys. data (m.p. ° C.) |
|---|---|---|---|---|---|
| 2.1. | CH | $OCH_3$ | $CH_3$ | 4-CN | |
| 2.2. | N | $OCH_3$ | $CH_3$ | 4-CN | |
| 2.3. | N | $NHCH_3$ | $CH_3$ | 4-CN | resin |
| 2.4. | N | $OCH_3$ | H | 4-CN | |

TABLE 2-continued

| No. | X | Y | $R_2$ | $R_3$ | phys. data (m.p. ° C.) |
|---|---|---|---|---|---|
| 2.5. | N | $OC_2H_5$ | H | 4-CN | |
| 2.6. | N | $NHCH_3$ | H | 4-CN | |

TABLE III

Intermediates III

| No. | $R_1$ | $R_2$ | $R_3$ | phys. data (m.p. ° C.) |
|---|---|---|---|---|
| 3.1. | $C_2H_5$ | $CH_3$ | 4-CN | |
| 3.2. | cyclopropyl | $CH_3$ | 4-CN | |

2. Formulation Examples for similar purposes of pesticidal use are descibed for example in WO 97/33890.

3. Biological Examples

In the following pathosystems the compounds of the table exhibit good activities.

EXAMPLE B-1

Action Against Puccinia Graminis on Wheat a) Residual-protective action 6 days after sowing, wheat plants are sprayed to drip point with an aqueous spray mixture (0.02% active ingredient), prepared from a wettable powder formulation of the active ingredient, and infected 24 hours later with a uredospore suspension of the fungus. After an incubation period of 48 hours (conditions: 95–100% relative humidity at 200), the plants are placed in a greenhouse at 220. Fungus infestation is evaluated 12 days after infection. In this test compounds 1.3 of Table 1 and 2.3 of Table 2 showed an efficacy of 80% or more.

b) Systemic action 5 days after sowing, wheat plants are watered with an aqueous spray mixture (0.006% active ingredient, based on the volume of the soil), prepared from a wettable powder formulation of the active ingredient. Care is taken that the spray mixture does not come into contact with parts of the plants that are above the soil. The plants are infected 48 hours later with a uredospore suspension of the fungus. After an incubation period of 48 hours (conditions 95–100% relative humidity at 200), the plants are placed in a greenhouse at 220. Fungus infestation is evaluated 12 In this test compounds 1.3 of Table 1 and 2.3 of Table 2 showed an efficacy of 80% or more.

EXAMPLE B-2

Action Against Phylophthora Infestans on Tomatoes a) Residual-protective action

After a cultivation period of three weeks, tomato plants are sprayed to drip point with an aqueous spray mixture (0.02% active ingredient), prepared from a wettable powder formulation of the active ingredient, and infected 24 hours later with a sporangia suspension of the fungus. Fungus infestation is evaluated 5 days after infection, a relative humidity of 90 to 100% and a temperature of 20° having been maintained during that period.

In this test compounds 1.3 of Table 1 showed an efficacy of 90% or more.

b) Systemic action

After a cultivation period of three weeks, tomato plants are watered with an aqueous spray mixture (0.006% active ingredient, based on the volume of the soil) prepared from a wettable powder formulation of the active ingredient. Care is taken that the spray mixture does not come into contact with parts of the plants that are above the soil. After 48 hours, the plants are infected with a sporangia suspension of the fungus. Fungus infestation is evaluated 5 days after infection, a relative humidity of 90 to 100% and a temperature of 20° having been maintained during that period. In this test compound 1.3 of Table 1 showed an efficacy of 80% or more.

EXAMPLE B-3

Action Against PlasmoPara Viticola on Vines

Vine seedlings at the 4- to 5-leaf stage are sprayed to drip point with an aqueous spray mixture (0.02% active ingredient), prepared from a wettable powder formulation of the active ingredient, and infected 24 hours later with a sporangia suspension of the fungus. Fungus infestation is evaluated 6 days after infection, a relative humidity of 95 to 100% and a temperature of 20° having been maintained during that period.

In this test compound 1.3 of Table 1 and 2.3 of Table 2 showed an efficacy of more than 95%.

EXAMPLE B-4

Residual-Drotective Action Against Venturia Inaegualis on Apples

Apple cuttings with 10–20 cm long fresh shoots are sprayed to drip point with an aqueous spray mixture (0.02% active ingredient), prepared from a wettable powder formulation of the active ingredient, and infected 24 hours later with a conidia suspension of the fungus. The plants are incubated for 5 days at 90–100% relative humidity and placed in a greenhouse for a further 10 days at 20–24°. Fungus infestation is evaluated 12 days after infection.

In this test compound 1.3 of Table 1 and 2.3 of Table 2 showed an efficacy of more than 95%.

EXAMPLE B-5

Action Against Ervsiphe Graminis on Barley a) Residual-Protective action

Barley plants about 8 cm in height are sprayed to drip point with an aqueous spray mixture (0.02% active ingredient), prepared from a wettable powder formulation of the active ingredient, and dusted 3 to 4 hours later with conidia of the fungus. The infected plants are placed in a greenhouse at 22°. Fungus infestation is evaluated 12 days after infection.

In this test compounds 1.3 of Table 1 and 2.3 of Table 2 showed an efficacy of 90% or more.

b) Systemic action

Barley plants about 8 cm in height are watered with an aqueous spray mixture (0.002% active ingredient, based on the volume of the soil) prepared from a wettable powder formulation of the active ingredient. Care is taken that the spray mixture does not come into contact with parts of the plants that are above the soil. The plants are dusted 48 hours later with conidia of the fungus. The infected plants are placed in a greenhouse at 22°. Fungus infestation is evaluated 12 days after a infection.

In this test compounds 1.3 of Table 1 and 2.3 of Table 2 showed an efficacy of 80% or more.

What is claimed is:

1. A compound of formula I

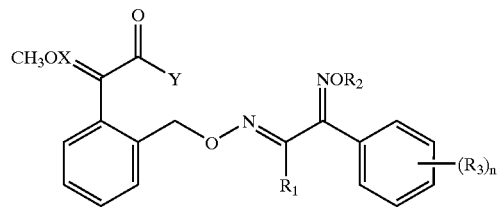

wherein a) X is CH, and Y is $OCH_3$, or
b) X is N, and Y is $OCH_3$, $OC_2H_5$ or $NHCH_3$;
   $R_1$ is ethyl or cyclopropyl;
   $R_2$ is hydrogen, methyl or ethyl;
   $R_3$ is cyano;
   n is 1 or 2.

2. A composition for controlling fungi which comprises, as active ingredient, an effective amount of a compound according to claim 1 together with a suitable carrier material.

3. A method of controlling and preventing infestation of plants by phytopathogenic fungi, which comprises applying a compound according to claim 1 to the plants, their parts or their environment.

* * * * *